(12) United States Patent
Li

(10) Patent No.: US 9,078,430 B2
(45) Date of Patent: Jul. 14, 2015

(54) CELL PREPARATION METHOD

(71) Applicant: Albert Li, Columbia, MD (US)

(72) Inventor: Albert Li, Columbia, MD (US)

( * ) Notice: Subject to any disclaimer, the term of this patent is extended or adjusted under 35 U.S.C. 154(b) by 143 days.

(21) Appl. No.: 14/022,722

(22) Filed: Sep. 10, 2013

(65) Prior Publication Data

US 2015/0072423 A1 Mar. 12, 2015

Related U.S. Application Data

(60) Provisional application No. 61/702,335, filed on Sep. 18, 2012.

(51) Int. Cl.
*A01N 1/02* (2006.01)

(52) U.S. Cl.
CPC ............ *A01N 1/0221* (2013.01); *A01N 1/0284* (2013.01)

(58) Field of Classification Search
None
See application file for complete search history.

(56) References Cited

U.S. PATENT DOCUMENTS

| 5,895,745 | A * | 4/1999 | Chandler et al. ................ 435/2 |
| 7,604,929 | B2 * | 10/2009 | Dryden et al. ................ 435/1.1 |
| 2013/0130374 | A1 * | 5/2013 | Powers et al. ................ 435/350 |

* cited by examiner

*Primary Examiner* — Robert Yamasaki
(74) *Attorney, Agent, or Firm* — McNeely, Hare & War LLP; Kevin J. McNeely

(57) ABSTRACT

A method of thawing cryopreserved human hepatocytes and cryopreserving the hepatocytes a second time without losing viability is described. It allows the preparation of cryopreserved human hepatocytes pooled from multiple donors by thawing the hepatocytes from the individual donors, combining the cells to form pooled hepatocytes, and recryopreserving the pooled hepatocytes. The method involves the thawing of the hepatocytes from the individual donors, maintaining the thawed hepatocytes at a low temperature that is above freezing temperature (e.g., 4° C.), and refreezing the thawed cells without further manipulation. The method allows the cryopreserving the human hepatocytes a second time after thawing, with viability similar to that after one single cryopreservation. This high efficiency method can be used for the preparation of highly viable pooled human hepatocytes for experimentation to minimize individual variations.

8 Claims, 1 Drawing Sheet

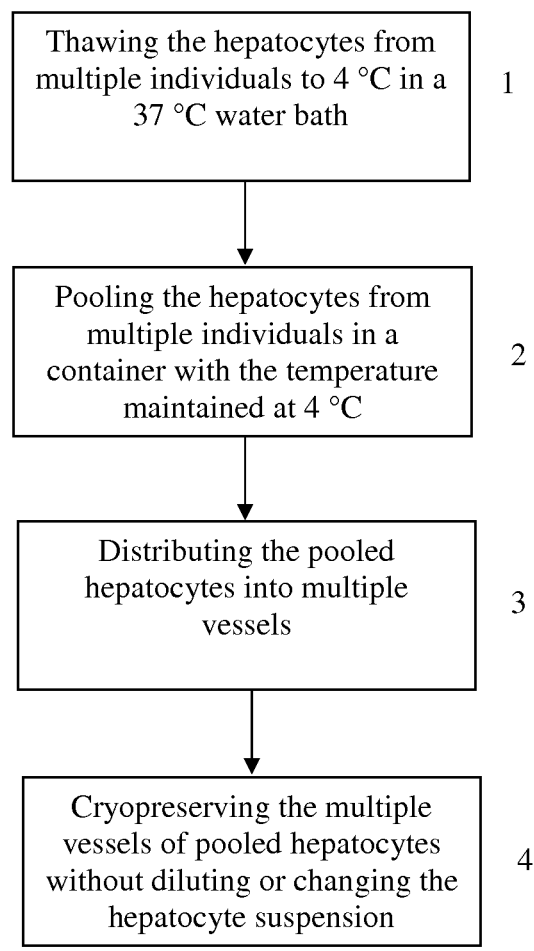

CELL PREPARATION METHOD

CROSS-REFERENCE TO RELATED APPLICATIONS

This utility patent application filed under 35 USC §111 claims priority to U.S. provisional patent application 61/702,335 filed on Sep. 18, 2012, which is incorporated by reference herein.

TECHNICAL FIELD

The field of the invention generally relates to novel methods for the preparation of cryopreserved hepatocytes, in particular, isolated liver parenchymal cells (hepatocytes).

BACKGROUND

The parenchymal cells of the liver, generally called hepatocytes, are the major cell types responsible for drug metabolism and are the cells damaged by hepatotoxicants. These cells therefore represent a desirable experimental system for the evaluation of drug metabolism and hepatotoxicity. There are numerous scientific publications on such application of hepatocytes in drug development.

A major problem with drug development is that a large number of drug candidates would fail in the clinic due to nonefficacy or adverse effects, even though drug candidates chosen for clinical trials are selected after extensive research in preclinical studies using laboratory animals and are found to have acceptable efficacy and safety. One of the major reasons is species differences, namely, that human drug effects may not always be the same as that found in laboratory animals.

One of the major species differences is drug metabolism. It is now known that human and nonhuman animals differ in multiple drug metabolizing enzyme pathways, with the most important being differences in P450 monooxygenases. The differences in enzyme pathways cause differences in metabolic fate of a xenobiotic. A drug can be toxic to humans and not to laboratory animals if the toxicity is caused by metabolites that are formed only in humans. Conversely, a drug can be toxic to animals but not in humans if the toxic metabolites are animal specific and are not formed in human.

Hepatocytes isolated from laboratory animals and human therefore represent important experiment systems for the evaluation of possible species differences in drug metabolism and toxicity. The use of hepatocytes is further made practical by successes in cryopreservation. Cryopreserved hepatocytes allow scientists to perform studies with hepatocytes simply by thawing and using the cells, avoiding the time-consuming isolation procedures. Cryopreserved hepatocytes, both from animals and humans, are now available commercially for use in research.

Individual differences between humans in drug metabolism are an established phenomenon. The differences can be caused by genetic and environmental factors. Hepatocytes from one individual can be substantially different from another individual. To aid "normalization" of the individual differences, human-based drug metabolism systems often involve materials combined from different individuals. For instance, one of the major experiment systems for the evaluation of drug metabolism, human liver microsomes, are often prepared from multiple human livers. This approach has been recently extended to human hepatocytes.

A typical procedure to thaw, pool, and re-freeze hepatocytes requires dilution of the cryopreservation medium followed by centrifugation through a high density medium to enrich for viable cells before the second freezing. These can be a laborious procedure.

SUMMARY

A method for the preparation of cryopreserved hepatocytes pooled from previously cryopreserved cells is described. In part, the novelty of the method is the thawing, pooling and re-cryopreservation of the hepatocytes without the conventional procedures of firstly dilution of the cryopreserving medium and enrichment of viable cells by iso-density centrifugation.

With this novel procedure, previously cryopreserved hepatocytes isolated from individual donors are stored in liquid nitrogen or a freezer maintained at approximately −150 degrees Celsius (° C.). To prepare cryopreserved hepatocytes pooled from multiple donors, the hepatocytes from individual donors are thawed in a 37° C. water bath only until the ice crystal just disappears (with the thawed solution at approximately 4° C. The thawed hepatocytes are maintained in an ice-bath set at approximately 4° C. The hepatocytes from multiple donors are placed together (pooled) into a container in the ice bath. After hepatocytes from all donors are added to the pool, the hepatocyte suspension containing cells from multiple donors is distributed into multiple cryogenic vials for cryopreservation. The "pooled" cryopreserved hepatocytes are stored in a liquid nitrogen freezer or a freezer maintained at approximately −150° C. The cryopreserved "pooled" hepatocytes can be thawed and used for experimentation using conventional procedures.

In one general aspect, a method for preparing cryopreserved human hepatocytes consisting of hepatocytes from multiple individuals without centrifugation includes cryopreserving hepatocytes from livers of multiple individuals in a hepatocyte suspension in separate vessels for each of the multiple individuals; thawing the vessels of the hepatocytes from multiple individuals in a 37° C. water bath until the hepatocyte suspension reaches a temperature of approximately 4° C. only until ice crystals in the hepatocyte suspension just disappear; pooling vessels of the hepatocytes from multiple individuals in a container with the temperature of the hepatocyte suspension maintained at a temperature of approximately 4° C.; distributing the pooled hepatocytes into multiple vessels; and cryopreserving the multiple vessels of pooled hepatocytes without diluting or changing the hepatocyte suspension.

Embodiments may include one or more of the following features. For example, the hepatocyte suspension may include a cryoprotectant such as, for example, Dulbecco's Modified Eagle Medium: Nutrient Mixture F-12 (DMEM/F12) medium supplemented with 10% fetal calf serum and 10% dimethyl sulfoxide (DMSO). The isolated hepatocytes may be from livers of multiple individuals.

The cryopreservation of the hepatocytes may include reducing the temperature to about −70° C. at a rate of about −1° C/min. The cryopreserved pooled hepatocytes may be stored in a cryogenic storage system at, for example, a temperature of about −150° C. or cooler. The cryopreserved pooled hepatocytes are thawed at a later time for experimentation.

DESCRIPTION OF THE DRAWINGS

FIG. 1 is a schematic of a novel procedure of thawing and pooling of cryopreserved hepatocytes from individual donors and distribution of the pooled hepatocytes for cryopreservation.

DETAILED DESCRIPTION

The inventor has developed an improved method for the preparation of cryopreserved human hepatocytes pooled from multiple donors. The method involves the isolation and cryopreservation of hepatocytes from multiple individuals. The isolated and cryopreserved hepatocytes are stored in a cryopreservation bank. Upon the collection of hepatocytes from multiple individuals, the hepatocytes are thawed, pooled, and re-cryopreserved using the improved method.

Elements of the improved method are to thaw the hepatocytes quickly at 37° C. to minimize ice crystal formation and the accompanied cellular damage, maintenance of the thawed hepatocytes at approximately 4° C., pooling of the hepatocytes from individual donors at approximately 4° C., distribution of the pooled hepatocytes into multiple containers ("cryovials") for cryopreservation, and cryopreservation. This novel method eliminates the multiple, laborious, and damaging steps of diluting the cryopreservant, centrifugation through an isotonic density gradient to enrich for viable cells, resuspension of the cell pellet in cryopreservant, pooling of the hepatocytes from multiple donors, distribution of the pooled hepatocytes into cryovials, and recryopreservation.

As in humans in vivo, the liver cells (hepatocytes) are the cells where drug metabolism occurs. Therefore, human hepatocytes in a culture represent a physiologically relevant model for the evaluation of drug metabolism and drug toxicity. To obtain the hepatocytes, the cells are isolated from liver tissue and then preserved using cryopreservation.

One of the other aspects of the invention is the collection of hepatocytes from various individuals. These hepatocytes are obtained from the liver tissues that have been procured for liver transplantation but not used due to the lack of appropriate recipients. In the United States, several organizations, e.g., International Institute For The Advancement of Medicine (IIAM) and National Development Research Institute (NDRI) specialize in the distribution of human livers to research laboratories.

The hepatocytes are stored in a cryopreservation bank and the cryopreserved cells later can be thawed for experimentation. It is known that there are substantial individual differences in hepatocyte properties, especially in drug metabolizing capacity. To allow the generation of results to represent the "normalized" human population, a mixture of hepatocytes (pooled hepatocytes) from multiple individuals are used. The conventional procedure includes thawing hepatocytes that were previously cryopreserved from individual donors, dilution to minimize cryopreservant toxicity, centrifugation to collect the hepatocytes, density gradient separation of viable and non-viable cells/cell debris, suspension of the purified cells in cryopreservant, distribution in cryovials, and recryopreservation. These steps are time-consuming and labor-intensive due to the various dilution and centrifugation steps.

A novel method is invented here for the preparation of cryopreserved pooled human hepatocytes. With this novel method, the individually cryopreserved human hepatocytes are thawed, pooled, distributed in cryovials, and recryopreserved. The multiple centrifugation steps, the density gradient, and the use of new cryopreservant are eliminated.

Procedures for the preparation of pooled cryopreserved human hepatocytes from multiple individuals are shown in FIG. 1 and set forth in the following operations:

1. Vials of cryopreserved human hepatocytes from multiple individual patients were thawed by immersion in water in a waterbath maintained at 37° C. As soon as the ice crystals disappear, the vials are placed in an ice-bath maintained at 4° C.

2. The hepatocytes are recombined (pooled) by removal from the vials into a glass beaker in an ice-bath maintained at 4° C.

3. The pooled hepatocytes are redistributed using a pipette into multiple vials for a second cryopreservation. No centrifugation or cell purification is performed.

4. The vials of pooled hepatocytes are cryopreserved in a programmable freezer at a constant rate of freezing, particularly about −1° C./minute until a suitable low temperature, particularly about −70° C. or lower, is reached. The cryopreserved cells are stored at a suitable temperature, particularly about −150° C. or lower, using a suitable apparatus, particularly a liquid nitrogen cryogenic storage system.

For experimentation with the cryopreserved pooled hepatocytes, each vial of hepatocytes is removed from liquid nitrogen cryogenic storage, thawed in a 37° C. water bath, and centrifuge at 100×g for 10 minutes in 50 mL of Cryopreserved Hepatocytes Recovery Medium (CHRM; APSciences Inc., Columbia, Md.). The resulting pellet can be resuspended and used for experimentation.

EXAMPLES

1. Human hepatocytes isolated and cryopreserved from six individuals were thawed in a waterbath till the ice crystals disappeared and immediately placed in an ice bath maintained at approximately 4° C. The thawed hepatocytes were cryopreserved a second time using a control rate freezer programmed at approximately −1 degree per minute until −90° C. The hepatocytes were stored in liquid nitrogen for 7 days. The hepatocytes from the initial cryopreservation and the second cryopreservation were thawed in a 37° C. waterbath, recovered by centrifugation through Cryopreserved Hepatocytes Recovery Medium (APSciences Inc.), resuspended in culture medium, and viability determined by trypan blue exclusion. The following results were observed:

| Hepatocytes | Viability ($1^{st}$ cryopreservation) | Viability ($2^{nd}$ cryopreservation) |
| --- | --- | --- |
| Donor 1 | 92% | 88% |
| Donor 2 | 94% | 95% |
| Donor 3 | 86% | 86% |
| Donor 4 | 76% | 77% |
| Donor 5 | 96% | 94% |
| Donor 6 | 88% | 76% |

The results showed that the novel method allows human hepatocytes to be recovered from cryopreservation, followed by a second cryopreservation, without apparent loss of—viability. This success suggest that hepatocytes from multiple individuals can be thawed, pooled and re-cryopreserved.

2. Human hepatocytes isolated and cryopreserved from eight individuals were thawed in a waterbath till the ice crystals disappeared and immediately placed in an ice bath maintained at approximately 4° C. The thawed hepatocytes were pooled, distributed into new cryovials and cryopreserved a second time using a control rate freezer programmed at approximately −1 degree per minute until −90° C. The pooled hepatocytes were stored in liquid nitrogen for 7 days. The cryopreserved pooled hepatocytes were thawed in a 37° C. waterbath, recovered by centrifugation through Cryopreserved Hepatocytes Recovery Medium (APSciences Inc.), resuspended in culture medium, and viability determined by trypan blue exclusion. The viability was determined to be 91%. The results therefore suggest that cryopreserved human hepatocytes pooled from multiple donors can be prepared using the invention.

What is claimed is:

1. A method for preparing cryopreserved human hepatocytes pooled from multiple individuals without centrifugation, the method comprising:

cryopreserving human hepatocytes from livers of multiple individuals in hepatocyte suspension media in separate vessels for each of the multiple individuals;

thawing the vessels of the hepatocytes from multiple individuals in a 37° C. water bath until the hepatocyte suspension media reaches a temperature of approximately 4° C. and maintaining the hepatocyte suspension media at 4° C. until ice crystals in the hepatocyte suspension just disappear;

pooling the thawed hepatocytes from the separate vessels of the multiple individuals in a container while maintaining the temperature of the hepatocyte suspension media at approximately 4° C.;

distributing the pooled hepatocytes into multiple vessels; and cryopreserving the multiple vessels of pooled hepatocytes, wherein the method does not involve diluting or changing the hepatocyte suspension media or subjecting the hepatocytes to centrifugation.

2. The method of claim 1, wherein the hepatocyte suspension media comprises a cryoprotectant.

3. The method of claim 2, wherein the cryoprotectant comprises Dulbecco's Modified Eagle Medium: Nutrient Mixture F-12 (DMEM/F12) medium supplemented with 10% fetal calf serum and 10% dimethyl sulfoxide (DMSO).

4. The method of claim 1, wherein cryopreserving the hepatocytes comprises cryopreserving the hepatocytes to a temperature of about −70° C. at a rate of about −1° C./min.

5. The method of claim 1, further comprising storing the cryopreserved pooled hepatocytes in a cryogenic storage system.

6. The method of claim 5, wherein storing the hepatocytes comprises storing at a temperature of about −150° C. or cooler.

7. The method of claim 1, further comprising isolating the hepatocytes from livers of multiple individuals.

8. The method of claim 1, further comprising thawing of the cryopreserved pooled hepatocytes for experimentation.

* * * * *